US008428968B2

(12) United States Patent
Bellam et al.

(10) Patent No.: US 8,428,968 B2
(45) Date of Patent: Apr. 23, 2013

(54) INTERACTIVE SYSTEM FOR PATIENT ACCESS TO ELECTRONIC MEDICAL RECORDS

(75) Inventors: Sashidhar Bellam, Madison, WI (US); Sumit Rana, Madison, WI (US); Davin Sannes, Mount Horeb, WI (US); Bhavik Shah, Madison, WI (US); Sapan Anand, Madison, WI (US); Christy Benson, Madison, WI (US); Matthew Sidney, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 2200 days.

(21) Appl. No.: 10/842,080

(22) Filed: May 10, 2004

(65) Prior Publication Data

US 2005/0251423 A1 Nov. 10, 2005

(51) Int. Cl.
*A61B 5/00* (2006.01)
*G06F 19/00* (2006.01)

(52) U.S. Cl.
USPC ............................................................ 705/3

(58) Field of Classification Search .................. 705/2, 3
See application file for complete search history.

(56) References Cited

U.S. PATENT DOCUMENTS

| | | | |
|---|---|---|---|
| 4,591,974 A | 5/1986 | Dornbush et al. | |
| 4,667,292 A | 5/1987 | Mohlenbrock et al. | |
| 4,839,806 A | 6/1989 | Goldfischer et al. | |
| 4,893,270 A | 1/1990 | Beck et al. | |
| 4,962,475 A | 10/1990 | Hernandez et al. | |
| 5,072,383 A | 12/1991 | Brimm et al. | |
| 5,072,412 A | 12/1991 | Henderson, Jr. et al. | |
| 5,072,838 A | 12/1991 | Price, Jr. et al. | |
| 5,077,666 A | 12/1991 | Brimm et al. | |
| 5,088,981 A | 2/1992 | Howson et al. | |
| 5,101,476 A | 3/1992 | Kukla | |
| 5,253,362 A | 10/1993 | Nolan et al. | |
| 5,301,105 A | 4/1994 | Cummings, Jr. | |
| 5,319,543 A | 6/1994 | Wilhelm | |
| 5,325,478 A | 6/1994 | Shelton et al. | |
| 5,361,202 A | 11/1994 | Doue | |
| 5,428,778 A | 6/1995 | Brookes | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,692,125 A | 11/1997 | Schloss et al. | |

(Continued)

FOREIGN PATENT DOCUMENTS

| | | |
|---|---|---|
| WO | WO 96/27163 | 9/1996 |
| WO | WO 98/13783 | 4/1998 |

(Continued)

OTHER PUBLICATIONS

Acute Software, "Sun Solutions Catalog", 12 pages.

(Continued)

*Primary Examiner* — Gerald J. O'Connor
*Assistant Examiner* — Trang Nguyen
(74) *Attorney, Agent, or Firm* — Boyle Fredrickson, S.C.

(57) ABSTRACT

A programmable rules-based interface between a patient and an electronic medical record EMR allows controlled patient access to the EMR allowing increased patient participation in the healthcare process.

37 Claims, 2 Drawing Sheets

U.S. PATENT DOCUMENTS

| | | | |
|---|---|---|---|
| 5,724,584 A | 3/1998 | Peters et al. | |
| 5,748,907 A | 5/1998 | Crane | |
| 5,751,958 A | 5/1998 | Zweben et al. | |
| 5,760,704 A | 6/1998 | Barton et al. | |
| 5,772,585 A | 6/1998 | Lavin et al. | |
| 5,778,346 A | 7/1998 | Frid-Nielson et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,838,313 A | 11/1998 | Hou et al. | |
| 5,845,253 A | 12/1998 | Rensimer et al. | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,915,240 A | 6/1999 | Karpf | |
| 5,924,074 A | 7/1999 | Evans | |
| 5,946,659 A | 8/1999 | Lancelot et al. | |
| 5,983,210 A | 11/1999 | Imasaki et al. | |
| 5,997,446 A | 12/1999 | Stearns | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,037,940 A | 3/2000 | Schroeder et al. | |
| 6,047,259 A | 4/2000 | Campbell et al. | |
| 6,063,026 A | 5/2000 | Schauss et al. | |
| 6,067,523 A | 5/2000 | Bair et al. | |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,188,988 B1 | 2/2001 | Barry et al. | |
| 6,263,330 B1 | 7/2001 | Bessette | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 | 2/2002 | Cummings, Jr. et al. | |
| 6,401,072 B1 | 6/2002 | Haudenschild et al. | |
| 6,415,275 B1 | 7/2002 | Zahn | |
| 7,222,066 B1* | 5/2007 | Oon | 704/9 |
| 2001/0016056 A1 | 8/2001 | Westphal et al. | |
| 2001/0016853 A1 | 8/2001 | Kucala | |
| 2001/0039503 A1* | 11/2001 | Chan et al. | 705/2 |
| 2001/0039504 A1* | 11/2001 | Linberg et al. | 705/3 |
| 2001/0049610 A1 | 12/2001 | Hazumi | |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002535 A1 | 1/2002 | Kitchen et al. | |
| 2002/0007287 A1 | 1/2002 | Straube et al. | |
| 2002/0077865 A1* | 6/2002 | Sullivan | 705/3 |
| 2003/0078911 A1* | 4/2003 | Haskell et al. | 707/2 |
| 2003/0088440 A1* | 5/2003 | Dunn | 705/3 |
| 2003/0120516 A1* | 6/2003 | Perednia | 705/3 |
| 2003/0208381 A1* | 11/2003 | Walter et al. | 705/3 |

FOREIGN PATENT DOCUMENTS

| | | |
|---|---|---|
| WO | WO 99/22330 | 5/1999 |
| WO | WO 99/44162 | 9/1999 |
| WO | WO 99/63473 | 12/1999 |
| WO | WO 00/28460 | 5/2000 |
| WO | WO 00/29983 | 5/2000 |
| WO | WO 00/65522 | 11/2000 |

OTHER PUBLICATIONS

Andrew, et al., "Computer-based Patient Records—Venturing off the Beaten Path: It's Time to Blaze New CPR Trails", Healthcare Informatics, 17 pages, May 1997.
"Autonomy Update", Product Brief, 3 pages.
"Brio.Portal", Product Information sheet, 1 page.
"CDR-Web", Reliance Software Systems, 1 page, 2000.
"Census Management", DINMAR (U.S.) Inc., 2 pages, 2002.
Cerner, "Acute Care EMR Solutions", 2 pages.
"Clinician Documentation with EMR", CliniComp, Int, 1 page, 1999-2002.
"Clinician Documentation with EMR", ClinicComp, Intl., 1 page, 1999-2002.
CMRxp—Computerized Medical Records Powered by Experiencell, Electronic Medical Records (EMR)xp Experience, ChartCare Inc., 2 pages, Mar. 5, 2003.
"DR-InBasket-Lab Results, Messaging and To-Do's", ChartCare Inc., 3 pages, Mar. 5, 2003.
Eclipsys, Advanced Clinical Solutions, "Sunrise Knowledge-based Orders", 4 pages.
Eclipsys, Advanced Clinical Solutions, "Sunrise Clinical Manager", 4 pages.
Eclipsys, News & Events, Press Releases, 3 pages, Apr. 16, 2002.
"EMR Features", Care is #1, 1 page, 1999, 2000.
"Enterprise Systems Management", Cerner Technologies, 5 pages, 2001.
"Essentris(TM) CPOE", CliniComp, Intl., 2 pages, 1999-2002.
"Essentris(TM) GDR", CliniComp, Int., 2 pages, 1999-2002.
ExcelCare Windows, 2 pages
Expeditor Systems—The Patient Flow Systems Experts, 3 pages, 2001.
Grimson, et al., "Interoperability Issues in Sharing Electronic Healthcare Records—the Synapses Approach", IEEE, pp. 1o-185, 1997.
Hazumi, et al., "Development of Electronic Medical Record System", NEC Res. & Develop. 41(1):102-105, 2000.
HealthMatics(TM) Office, 3 pages.
IC-Chart Additional Modules, InteGreat Inc., 1 page, 2003.
IDX, "Foundation", 2 pages.
IDX, "Supporting the Work of Clinicians", 1 page.
InteGreat—IC-Chart(TM) Information, 1 page.
"Intensivist Tools", CliniComp, Intl., 2 pages, 1999-2002.
Johnson, "Today's CDRS: The Elusive 'Complete' Solutions", Healtcare Informatics, 7 pages, Jul. 1997.
"LabTrack-Lab Ordering & Results Tracking", LabTrack-Lab Result Tracking Software, ChartCare Inc., 3 pages, Mar. 5, 2003.
"Location of JMJ Technologies—EncounterPRO, The Workflow Enabled CPR/EMR from JMJ Technologies", 6 pages, www.jujtech.com.
"Managing Mail Messages with Rules", Microsoft Outlook Help Manual, 5 pages, Version 6.
Marietti, "O' Pioneers!", Healthcare Informatics, 9 pages, May 1999.
McDonald, et al., "The Regenstrief Medical Record System: A Quarter Century Experience", Inter. J. Med. Informatics 54:225-253, 1999.
McKesson, "Horizon Clinicals", 2 pages, Apr. 21, 2003.
Mercando, "Appointment Scheduling on Computer", PACE 20:1860-1862, 1997.
"PatInfo—Patient Information Handouts", PatInfo—Patient Demographics Software, ChartCare Inc., 2 pages, Mar. 5, 2003.
"Patient Lists", Epic Systems Corp., EpicCare Inpatient Electronic Medical Record Jul. 2000 User's Guide, Section 11.3-11.4, 3 pages.
"Portal-in-a-Box", Product Brief, 6 pages.
"Recall-Patient Health Maintenance", ChartCare Inc., 3 pages, Mar. 5, 2003.
"Rx-MedTrack-Prescription Writing/Medication Tracking", Rx-MedTrack-Prescription Writing Software, ChartCare Inc., 2 pages, Mar. 5, 2003.
"Services", InteGrate Inc., 2 pages, 2003.
"The Right Tools", Product Description, InteGreat Inc., 1 page, 2003.
"Working with Patient Lists", Epic Systems Corp., EpicCare Inpatient Electronic Medical Record Jul. 2000 Uer's Guide, Section 10.5-10.6, 3 pages.
Kaiser Permanente, Request of Cancer Appointments Online, 2 pages.

* cited by examiner

INTERACTIVE SYSTEM FOR PATIENT ACCESS TO ELECTRONIC MEDICAL RECORDS

CROSS-REFERENCE TO RELATED APPLICATIONS

Statement Regarding Federally Sponsored Research or Development

The present invention relates to electronic medical record (EMR) systems and in particular to an EMR system allowing access to and entry of data by a patient.

Enlisting patients as active participants in their own healthcare can increase patient satisfaction and the quality of the healthcare experience while decreasing the cost of providing that care.

A number of healthcare organizations and other enterprises have used the Internet to provide basic information to patients allow the scheduling of appointments, and to provide interactive healthcare calculators and the like which allow patient-sourced data to be input and certain information to be returned. While these services allow more patient involvement in the healthcare process, the information provided by and to the patient is held separate from the centralized electronic medical record (EMR) that provides a cohesive repository of medical information for doctors and other healthcare providers.

This isolation of the patient from the EMR is done for good reason. Preventing patients from entering data into the EMR preserves the validity of the EMR data so that it may be relied upon by other healthcare professionals. Patients often unfamiliar with the data they are collecting are likely more prone to make significant mistakes in that data entry than a healthcare provider.

Further, the data in the EMR, intended for healthcare professionals, is often unintelligible by patients and some aspects of the data could be confusing or unnecessarily alarming to a layperson. The act of a healthcare professional entering medical information is often the juncture at which the data is reviewed or considered by the healthcare professional in detecting possible problems. Entry of data by patients eliminates this important juncture. Finally, issues of medical privacy make it desirable to limit to the extent possible, broad access to the electronic medical record. Medical privacy laws prohibit medical data from being made available to the parties not authorized by the patient and some medical data from being made available to the patient except in the presence of a qualified healthcare professional.

This need to separate the patient from the integrating features of the EMR limits the ability to which the patient may significantly contribute to his or her healthcare.

BRIEF SUMMARY OF THE INVENTION

The present invention provides practical access by a patient to the information in his or her EMR, significantly improving communication between a patient and their healthcare organization. Critical to the invention is a set of administrator programmable rules based on data from the EMR that control this access, limiting access to certain data, interpreting the data for the patient as necessary, and marking data from the patient so as to indicate its accuracy and level of review. Access to the EMR data allows improved information to be provided to the patient by processing patient-sourced data according to information stored in the EMR to provide data range checking and trend analyses. The invention communicates with a healthcare provider so that patient-sourced data can be reviewed and health issues brought to the attention of the healthcare provider much as if the healthcare provider entered the data his or herself. This invention may allow direct patient/physician communication using secured messaging.

Specifically, the present invention in one embodiment provides an access program for an electronic medical record (EMR) system executing a stored program to receive patient-sourced medical data about a patient from the patient, process the patient-sourced medical data according to medical data about the patient held in the EMR, and return information based on the processed patient-sourced data to the patient.

It is thus one object of at least one embodiment of the invention to tap into the centralized EMR to allow improved communication of medical information to the patient, as well as from the patient to the provider. Unlike systems that provide the patient access to specialized patient-only databases, the present invention provides nearly unlimited flexibility in utilizing the full EMR used by healthcare providers as a comprehensive source of patient information.

The processing of the patient-sourced data may use historical data about the patient held in the EMR.

It is therefore one object of at least one embodiment of the invention to take advantage of time-linked data held in the EMR and to integrate patient-sourced data gathering with data gathering or validation by healthcare professionals.

The processing of the patient-sourced data provides data to the patient indicating a healthy range for the patient-sourced data based on medical data about the patient held in the EMR. Alternatively, or in addition, the processing of the patient-sourced medical data may include a testing step that checks the data for entry errors based on knowledge about the patient held in the EMR.

It is an object of at least one embodiment of the invention to provide sophisticated context for data provided to the patient based on the full EMR.

The access program may notify a healthcare professional of detected errors to permit review of the patient-sourced data. This notification may link the healthcare professional directly to the relevant patient-sourced data.

It is an object of at least one embodiment of the invention to promote patient involvement in medical data collection without jeopardizing the reliability of EMR data that may be relied upon by health care professionals.

The access program may include a web server and the patient-sourced data may be received over the Internet from a web browser. The patient-sourced data may be authenticated, for example, by means of a password or other authentication system.

It is thus another object of at least one embodiment of the invention to remove the barriers to patient participation in his or her healthcare delivery without jeopardizing patient privacy.

The access program may receive a patient request for access to medical data about the patient from the EMR and determine a permission level for the patient with respect to access of the data using administrator programmable rules receiving as an argument the type of data or the value of the data. Access of the data by the patient is allowed only if the patient has permission according to the programmable rules.

It is thus one object of at least one embodiment of the invention to provide flexible rules controlling access by a patient to his or her EMR.

The administrator programmable rules may change a permission of patient-sourced data written to the EMR to read-only permission after a predetermined period of time.

It is thus one object of at least one embodiment of the invention to limit the ability of a patient to revise data entered by the patient after a predetermined period of time and thus to preserve the function of the EMR as a historical record for justifying medical care decisions.

The access program may receive a patient request for medical data about the patient from the EMR and translate the data received from the EMR in response to the request from terminology appropriate to the medical profession to terminology appropriate to a layperson.

It is thus one object of at least one embodiment of the invention to allow a layperson access to and understanding of the EMR while allowing use of the EMR to convey precisely stated medical information between medical professionals.

The access program may receive patient-sourced medical data and associate that data with a tag distinguishing the patient-sourced data from data entered by a healthcare professional before entry of the tagged patient-sourced data into a central patient record system.

It is thus one object of at least one embodiment of the invention to provide an indication of patient-sourced data to healthcare professionals to preserve the integrity of the EMR data.

The access program for an electronic medical record may receive patient-sourced medical data and analyze the received data in light of other data stored in the EMR to determine a trend over time indicating a possible medical issue and notify a healthcare professional if a medical issue is indicated.

It is thus another object of at least one embodiment of the invention to introduce the physician into the chain of data entry between patient and EMR to preserve traditional physician oversight.

These particular objects and advantages may apply to only some embodiments falling within the claims and thus do not define the scope of the invention.

DETAILED DESCRIPTION OF THE PREFERRED EMBODIMENT

Figure 1:
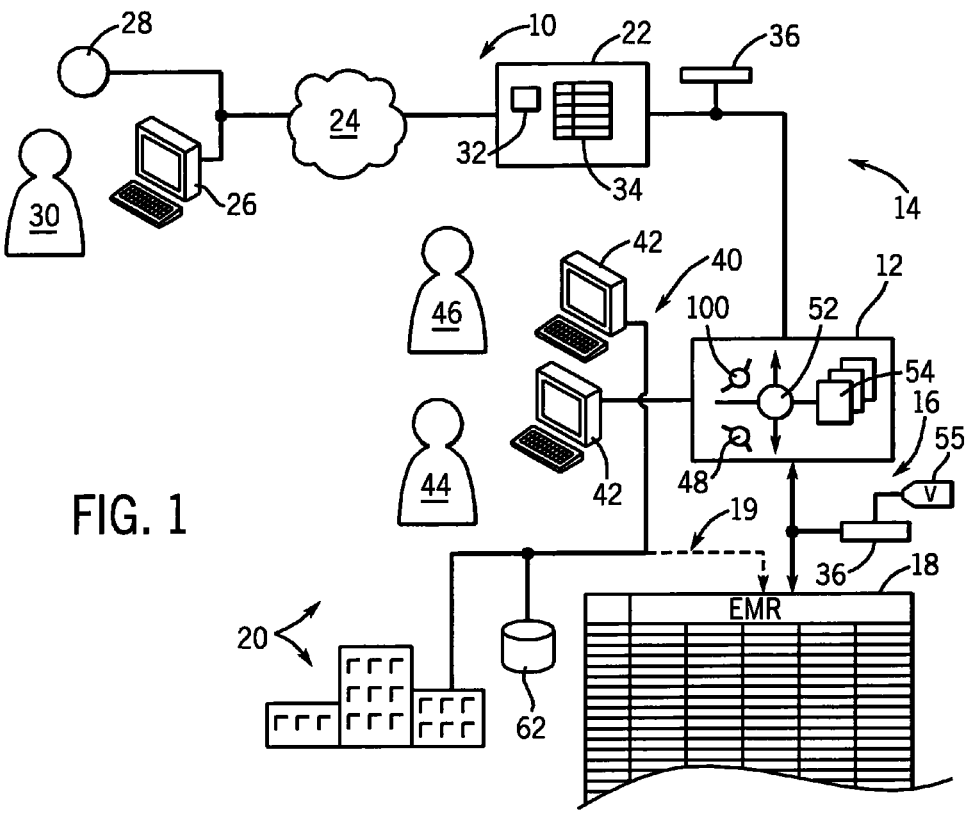
FIG. 1 is a simplified block diagram of an access program for an EMR providing an Internet communication channel.

Referring now to FIG. 1, a computerized access system 10 per the present invention may include an interface module 12 standing between a patient communication channel 14 and an EMR communication channel 16, the latter communicating with an electronic medical record (EMR) database 18. Generally the interface module 12 is a program that may be physically located on an independent computer or run on a computer shared with another function such as the EMR database 18.

Generally, the EMR database 18 includes a complete medical history of many patients collected from a variety of healthcare sources 20 including physicians and other healthcare professionals such members of the staff at hospitals, clinics, and laboratories communicating on standard EMR network 19. As will be understood to those of ordinary skill in the art, the EMR database 18 includes biographical information about the patient describing the patient, including but not limited to the patient's age, gender, height and weight, and medical history information including the patient's medical conditions, previous medical procedures, medications, and laboratory test results. The EMR database 18 may be centrally accessed by many different healthcare sources 20 and thus serves as a path of intercommunication among many individuals working together to deliver healthcare.

The EMR database 18 is depicted as a single logical flat file for simplicity but may be configured in any of a variety of well known database formats including relational database structure, object database structures and the like. The data of the EMR database 18, like all medical records, is protected under federal law to ensure that sensitive data of this record is not released in a way that would violate a patient's privacy rights. EMR databases may be obtained from a variety of commercial sources including Epic Systems Corporation, the assignee of the present invention, which sells an EMR database under the trade name of "Chronicles" used with the "EpicCare" and "Epicenter" electronic medical record software.

The patient communication channel 14 may join the interface module 12 to a web server 22 providing a secure socket layer connection to the Internet 24. The Internet 24 may in turn connect a number of patient terminals 26 (only one shown for clarity) implementing a browser and/or a communication port to a home monitoring system 28, either or both used by a patient 30.

The monitoring system 28 may be any of a number of different healthcare appliances, for example, a blood glucose monitor or a home dialysis system or other automated home healthcare providing a machine that can support Internet or other electronic data communication. Generally, the connection to the Internet 24 allows a means for the patient 30 to enter patient-sourced medical data into the computerized access system 10, the patient-sourced medical data being either machine-generated data from home monitoring system 28 or patient-collected data manually input by a patient into terminal 26. Patient sourced data will typically include without limitation selections from: patient's weight, blood glucose, blood pressure, pain level, previous health conditions, heart rate, temperature, last menstrual period, medications, and dialysis status.

The web server 22 includes a number of active web pages 32, some of which will be described below, allowing the patient and/or monitoring system 28 to transmit and receive data securely to and from the web server 22. Incorporated into these web pages 32, for example as a CGI script, is a program for authentication of the patient's access to the web pages 32. The authentication control program makes use of a log-in identifier/password validation table 34 both shown as logically held on the web server 22 but in the preferred embodiment stored and executed remotely. The login identifier/password validation table 34 holds one or more patient specific tokens (for example, log-in identifiers and passwords but possibly including instead or in addition biometric data and the like) that ensure access to possibly sensitive medical data is not freely available to unknown parties. The patient 30 may also allow access to his or her medical records by a proxy or patient's representative also stored as links in the log-in password/password validation table 34 which gives each proxy a unique token. Generally, the term "patient" as used herein should be considered to include the patient and/or the patient's proxies. One important proxy, of a parent for children, may be initiated as a reminder based on knowledge about childbirth from the EMR.

The patient 30 must enter the login identifier and password upon every new Internet communication session. The log-in identifier and password are not stored in cookie form on the patient terminal 26 such as might make anyone with access to the patient terminal 26 able to view or enter data on behalf of the patient 30. The monitoring system 28, however, may include a different internally encoded login identifier unique to that monitoring system 28 for the same purpose.

The table 34 may also include provisions allowing several different login identifiers and passwords to be associated with the same patient so that proxy access may be had by a patient's representative.

Data received by the web server 22 from the patient 30 is marked with a patient identification number and forwarded along the patient communication channel 14 as a patient identified message 36 possibly containing a request or patient sourced data to the interface module 12. Similar messages 36 may be received by the web server 22 along the patient communication channel 14 from the interface module and forwarded to the patient 30. Generally the messages 36 will be formatted to act as queries or responses to queries of or from the EMR database 18.

Referring still to FIG. 1, the interface module 12 may also connect to a provider communication channel 40 possibly using all or a portion of standard EMR network 19 allowing communication with healthcare sources 20 via terminals 42 associated, for example, with a primary care physician 44 and a system administrator 46. The physician 44 or administrator 46 may have access to the EMR database 18 directly per normal conventions to add, modify, read, or delete data, or through the interface module 12 as will be described using a viewer/editor 48.

Access through the interface module 12 by the physician 44 also provides limited access to the patient 30. In this respect, some patient-sourced data in messages 36 sent by the patient 30 can be routed to a physician 44 and messages from the physician 44 may be routed to the patient 30 in the form of secure communications. Such secure communications may also be initiated by the patient 30 as will be described further below.

Figure 2:
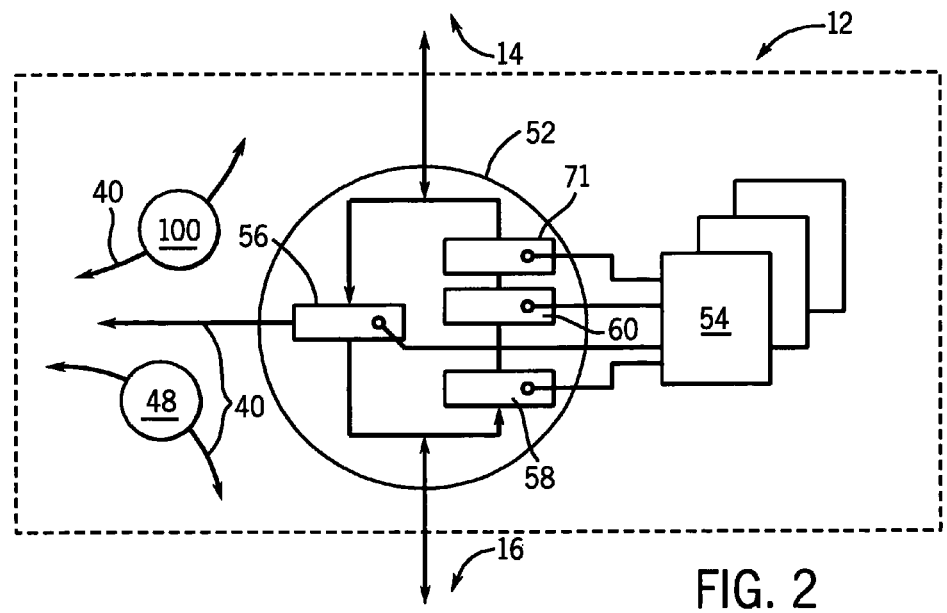
FIG. 2 is a detailed block diagram of the access program of FIG. 1 showing filters and routers moderating information flow according to user programmable rules.

Referring now to FIGS. 1 and 2, the interface module 12 employs a set of administrator programmable rules 54 to control the flow of data between the patient 30 and the EMR database 18 principally through rule engine 52. The administrator programmable rules 54 may be entered, modified, or deleted by the system administrator 46 for particular circumstances using a conventional editor program of a type well known in the art. Generally the rules are simple logical constructions describing test conditions and actions based on those test conditions as will be understood from the following discussion. The administrator in this case is considered to be an authorized individual other than the patient associated with a healthcare organization.

Generally, rule engine 52 includes a data entry filter 56 receiving data from the patient communication channel 14 and passing it to the EMR communication channel 16 and data reply filter 58 and translation program 60 and report generator 71 receiving data from the EMR communication channel 16 and passing it to the patient communication channel 14. Each of these filters and tables 56, 58, 60, and 71 applies administrator programmable rules 54 by accepting as rule arguments, the particular patient identified in a message 36 and one or more fields of the EMR database 18 being accessed for reading or writing and/or the data of those fields. User generated rules 54 can thus limit, modify or augment the data contained in messages 36 according to the type and value of data in the messages 36 and according to related data in the EMR database 18. In one example, the administrator programmable rules 54 provide the patient 30 with a controlled environment in which to view or modify records or the EMR database 18. In another example, data provided to the patient 30 may be subject to sophisticated processing, for example, trend analysis based on other data in the EMR database 18.

Figure 3:
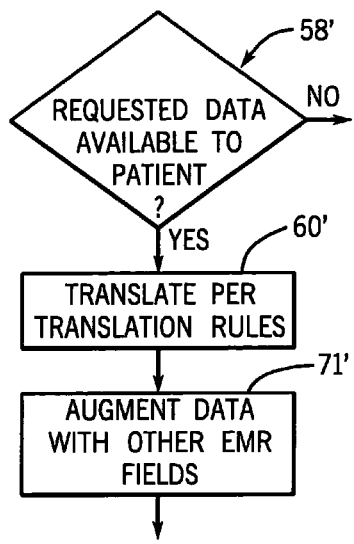
FIG. 3 is a flow chart showing the steps of data flow from the EMR to the patient.

Referring specifically to FIGS. 2 and 3, the data reply filter 58 reviews data from the EMR database 18 in response to a message 36 carrying information from the EMR database 18. At this step indicated by process block 58', the data reply filter 58 invested with administrator programmable rules 54 determines whether the requested data is to be available to the patient (or proxy-user) based on the data field or the data values themselves. The administrator programmable rules 54 may partition data of the EMR database 18 into data that may be viewed or not viewed by the patient 30. For example, nursing or progress notes may be blocked from being viewed by the patient generally regardless of their content. Alternatively or in addition, some fields of the EMR database 18 may be blocked depending on the content of the field. For example, the patient may be prohibited from viewing particular diagnoses or may have general ability to view lab tests except if the results of the test indicate that in-person consultation is to be preferred, for example, if a lab tests indicates an abnormal pap smear or HIV test. Certain data may be blocked simply to avoid clutter in the report (e.g., dates outside a certain date range) or to avoid needless distress to the patient (e.g., the patient may not wish to see they had breast cancer every time they review their problem list). The particular fields and values are determined flexible by the user programmable rules 54 and may be changed on a patient-by-patient basis. Further, data may be made generally available to patients, but an option may be given to the provider to block the data from patient access.

If permission is granted for the data to be received by the patient 30, the response message 36 containing the data proceeds to a translation program 60 which provides a set of patient-friendly words and phrases that may be substituted for words and phrases within the response message 36 to improve the intelligibility of the reply message to a layperson. The rules in this case simply effect a search and replace operation of a type well understood in the art as indicated by process block 60'. For example, a medical term such as "esophageal reflux" might be translated to "chronic heartburn" for a lay user by means of a series of search and replace type operations in the rules 54 or by selecting a different interpretation text for standard medical codes.

Data from the translation program 60 may be received by the report generator 71 which calls on other data from the EMR database 18 to augment the requested data of the message 36 or to put the requested data in context as indicated by process block 71'. For example, the report generator may prepare a chart comparing requested test results for the patient 30 to an ideal range based on patient-sourced data held in the EMR database 18 such as patient age, gender or other medical conditions. Alternatively, the report generator 71 may provide previously stored data to produce a time series putting the data in context. The report generator 71 may also provide the patient 30 with general patient information keyed to or tailored to the patient 30 based on the patient records, for example, general patient information about exercise geared to the patient's age or diet. This general patient information may be contained in a non-patient record file 62 as shown in FIG. 1 and provided by a third party vendor. This general patient information can also be triggered by the trend checker 66 which may help identify possible medical issues. The general patient information can include preprepared background information about the medical issue and clinical options for treatment.

Importantly, the report generator 71 may make use of data from the EMR database 18 not directly available to the patient. For example, a patient may be blocked from certain data related to the patient's mental health, but this information can be used to provide the patient with relevant content from the non-patient record file 62 including articles on dealing with stress or about counseling services. The report generator 71 may produce reminders, for example, for a pap smear, based on hidden data about sexual history. A report, for example, may show data about weight gain and cholesterol levels to encourage progress on these fronts, while hiding a diagnosis about obesity which might make the patient feel defeated.

Figure 4:
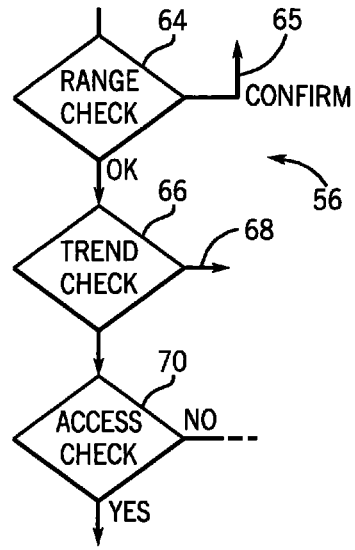
FIG. 4 is a flow chart similar to that of FIG. 3 showing the steps of data from the patient to the EMR.

Referring again to FIGS. 2 and 4, patient medical data coming from the patient 30 (patient-sourced data) is received by data entry filter 56 where it is first processed to determine that the patient-sourced data provided by the patient 30 objectively matches the particular range expected from that data per process block 64. Such patient-sourced data may include, for example, a patient's weight, blood glucose, blood pressure, and dialysis information for a dialysis machine. For example, a blood pressure entry by the patient may be checked against theoretically possible blood pressure entry values. If the value entered by the patient 30 does not fit within an expected range, a "request to confirm" message is sent as indicated by arrow 65. In response, the patient 30 may check and reenter that data. Alternatively, or in addition the range checking may flag the data for review by the physician 44 later who is also provided with a direct link to the data so that it may be easily examined and/or corrected. The patient-sourced data may be entered in response to a reminder message sent to the patient according to a stored reminder program as part of the computerized access system 10.

The range checking process block 64 may also request and receive from data in the EMR database 18, for example, data indicating recent similar data provided by the patient 30 to which the current data may be compared, or known medications taken by the patient 30 that might modify the range. Thus, the range checking may be invested with knowledge about the patient from the EMR database 18 including data that is not directly accessible to the patient.

If the patient 30 confirms the patient-sourced data or if the patient-sourced data passes the range checker 64, a data trend is checked per process block 66 which evaluates the data in light of other known data in the EMR database 18, for example, previous entries of data by the patient 30 and known medical conditions of the patient 30. Typically, trend checking will evaluate given patient-sourced data by extrapolating from previous data or other data in the EMR database 18. If the trend or simply an abnormal individual reading indicates a problem such as might require review by a healthcare professional, a message indicated by arrow 68 is provided to a physician 44 alerting them as to this trend which the healthcare professional might otherwise have noticed only by entering the data his or herself. The patient may be notified to seek an appointment and may be connected to a scheduling system or office.

Abnormal conditions detected by the trend checker can in addition notify the patient to call an emergency number or a provider on-call for immediate response, for example, significant change in blood pressure or heart rate as informed by data in the EMR database 18. Importantly, the trend checking can be informed by information about the patient obtained from the EMR database 18 as described by a rule 54. For example, a patient who has had congestive heart failure might be subject to a trend rule that is sensitive to a lower level of weight gain than is a person without such a condition. Likewise, a different trend rule might be used for a patient who has taken a medication (as indicated in the EMR database 18) that sometimes raises blood pressure or where a slight blood pressure rise signals a possible problem associated with the drug.

After the patient-sourced data has passed through the trend checking, process block 70 confirms that the patient-sourced data may be entered into the patient record of the EMR database 18. This access checker 70 is a logical construct and in fact normally implemented by activation of one or more web pages 32 allowing for particular data entry by the patient. A significant amount of the data of the EMR database 18 accessible to the patient will be read-only and in general, only a small subset of data will allow for data entry by the patient 30.

Figure 7:
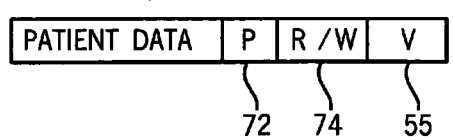
FIG. 7 is a logical diagram of patient-sourced data entered into the electronic medical record showing additional fields used for validation and control.

Referring now to FIG. 7, all patient-sourced data of message 36 entered into the EMR database 18 carries with it a patient-source tag 72 indicating that it is patient originated data. This patient-source tag 72 is always kept with the patient-sourced data to preserve the integrity of the EMR database 18. Nevertheless, the patient-sourced data is available freely to other users of the EMR database 18 to integrate the patient-sourced data with the healthcare system. The patient-sourced data of message 36 may also include a second read/write field 74 indicating whether the patient may continue to edit the data or whether it has become read-only data with respect to the patient. This read/write field may be carried with the data or may be enrolled in an administrator programmable rule 54 of the rule engine 52 and prevents delayed modification of data by the patient preserving data integrity. Normally data that may be written to (or modified) by the patient 30 is converted to read-only status after a predetermined period of time selected by an administrator 46. Finally, the patient-sourced data of message 36 may also include a validation tag 55 which may be provided optionally for data that has been validated by a healthcare professional indicating that it has additional reliability. This validation tag 55 may be attached by the physician 44 or administrator 46 using the viewer/editor 48 to review data from the patient after it has been enrolled in the EMR database 18 or as prompted by a message generated by rule engine 52. Importantly, the physician 44 does not need to recopy or re-enter the data, but may simply validate existing data.

Data within the EMR database 18 can be viewed in a number of ways based on these tags. Only validated data can be viewed or only invalidated, patient-sourced data may be viewed. Alternatively both types of data may be commingled with or without the tags being identified. In a third display method, the screen can be separated into a field reserved for each type of tagged data.

The patient-sourced data may be formatted by the web server 22 or the interface module to properly query the EMR database 18, in this case query referring both to operations of a standard query language including those that read, write, sort and search for data.

Figure 5:
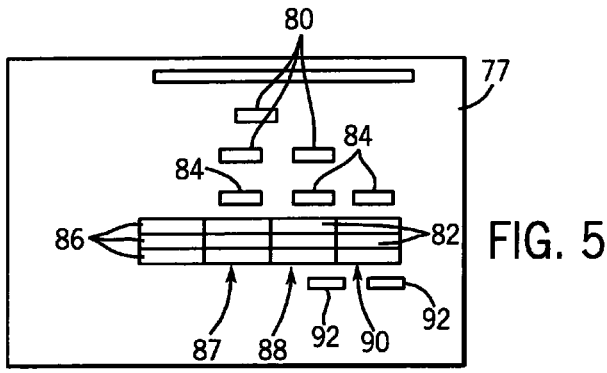
FIG. 5 is an example screen of an Internet browser displayed to the patient of FIG. 1 for the entry and editing of data.

Referring now to FIGS. 1 and 5, the entry of patient-sourced data by the patient 30 or the request and review of data from the EMR database 18 is facilitated by a data entry screen 77 generated by the browser on the patient terminal 26 from data provided by the web server 22. The data entry screen 77, for example, may provide data entry boxes 80 allowing the patient to designate data fields from the EMR database 18 for review or data for entry into particular fields of the EMR database 18 and data display fields 82 in which data from the EMR database 18 may be displayed. Data collected over a period of time may be indicated in tabular form with rows 86 being data types and columns being dates and times of the data per date flags 84 so that a first column 87 may allow for current data entry by the patient whereas later columns 88 and 90 may show previously entered data by the patient. An edit flag 92 may indicate whether the data is still editable by the patient (per read/write field 74) or whether it has reverted to a read only status. Triggers other than time, such as validation of the data or its range can be used in addition or instead based on programmable rules.

Figure 6:
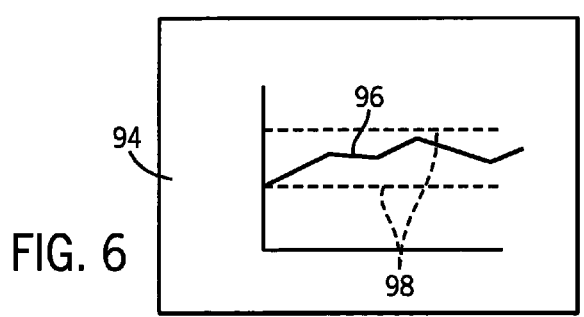
FIG. 6 is a screen similar to that of FIG. 5 showing an example representation of data provided to the patient.

Alternatively, data may be reviewed on a data review screen 94 as shown in FIG. 6. In this data review screen 94 shows a line plot 96 of previous data obtained from the EMR database 18 and normal bars 98 based on knowledge about the patient obtained from the patients EMR database 18. The patient, for example, may also view other aspects of the EMR database 18. For example, a history of prescriptions and their status or the results of previous office visits which may also be viewed by a proxy for example, a parent or guardian.

Referring again to FIG. 2, the present invention, providing communication with the patient 30 over the Internet 24, allows for secure communication between the patient 30 and physician 44 via a dedicated messaging server 100 contained within the interface module 12. Incorporation of the messaging system into the present invention allows the physician to review messages in light of data read or viewed from the EMR communication channel 16.

It is specifically intended that the present invention not be limited to the embodiments and illustrations contained herein, but include modified forms of those embodiments including portions of the embodiments and combinations of elements of different embodiments as come within the scope of the following claims.

We claim:

1. A computer-implemented electronic medical record (EMR) access control system configured to implement an access program stored on a computer-readable medium comprising:
   a computer, which when controlled by the access control program, is configured to:
   a) receive patient-sourced medical data about a patient from the patient at a computer system;
   b) determine a patient specific range of physiology values based at least in part on the patient-sourced medical data;
   c) generate a revised patient specific range of physiology values using the access program based on a computer-implemented electronic medical record system of a healthcare provider using a subset of the data in the electronic medical record of the healthcare provider, the subset being defined by the healthcare provider;
   e) compare the revised patient specific range of physiology values to the patient-sourced medical data using the access program to generate an information report based on the medical record data in the electronic medical record of the healthcare provider; and
   f) return the information report to the patient based on the comparison,
   wherein the subset defined by a healthcare provider is defined to exclude patient access to information in the electronic medical record of the healthcare provider until the occurrence of a personal consultation between the patient, and the healthcare provider, the exclusion being indicated by data and programmable rules in the electronic medical record of the healthcare provider.

2. The computer-implemented electronic medical record (EMR) access control system of claim 1 wherein determining a patient specific range of physiology values uses historical data about the patient held in the electronic medical record of the healthcare provider.

3. The computer-implemented electronic medical record (EMR) access control system of claim 1 wherein determining a patient specific range of physiology values includes testing the data for entry errors based on knowledge about the patient held in the electronic medical record of the healthcare provider.

4. The computer-implemented electronic medical record (EMR) access control system of claim 3 wherein the patient is notified of the entry errors to permit re-entry of the patient-sourced medical data.

5. The computer-implemented electronic medical record (EMR) access control system of claim 1 wherein returning the information report includes providing output to the patient indicating a medical issue.

6. The computer-implemented electronic medical record (EMR) access control system of claim 5 wherein the computer provides the patient with prepared background information about the medical issue.

7. The computer-implemented electronic medical record (EMR) access control system of claim 5 wherein the computer provides the patient with clinical options for assisting in correcting the medical issue.

8. The computer-implemented electronic medical record (EMR) access control system of claim 5 wherein the patient is prompted to seek healthcare support.

9. The computer-implemented electronic medical record (EMR) access control system of claim 1 wherein a healthcare professional is notified of abnormal conditions indicated by the patient-sourced data to permit review of the patient-sourced data.

10. The computer-implemented electronic medical record (EMR) access control system of claim 9 wherein the healthcare professional is notified by a secure electronic message.

11. The computer-implemented electronic medical record (EMR) access control system of claim 1 wherein the patient-sourced data is selected from the group consisting of: patient's weight, blood glucose, blood pressure, pain level, previous health conditions, heart rate, temperature, last menstrual period, and dialysis status.

12. The computer-implemented electronic medical record (EMR) access control system of claim 1 wherein the patient-sourced data from the patient is authenticated by a patient specific token.

13. The computer-implemented electronic medical record (EMR) access control system of claim 1 wherein the electronic medical record of the healthcare provider holds medical data provided by different healthcare professionals for multiple patients.

14. The computer-implemented electronic medical record (EMR) access control system of claim 1 wherein the access control program includes a web server and the patient-sourced data is received over the Internet from a web browser.

15. The computer-implemented electronic medical record (EMR) access control system of claim 1 wherein the patient-sourced data is entered into the electronic medical record of the healthcare provider.

16. The computer-implemented electronic medical record (EMR) access control system of claim 15 wherein the patient-sourced data is further presented to a healthcare professional for validation prior to being entered into the electronic medical record of the healthcare provider.

17. The computer-implemented electronic medical record (EMR) access control system of claim 1 wherein patient-sourced data is selected from a source consisting of: machine-generated data from home healthcare appliances and patient-collected data manually input by a patient.

18. The computer-implemented electronic medical record (EMR) access control system of claim 1 wherein the subset defined by a healthcare provider is defined to exclude patient access to information pertaining to at least one medical condition identified by the programmable rules as being known to cause distress to the patient.

19. A computer-implemented electronic medical record (EMR) access control system configured to implement an access program stored on a computer-readable medium comprising:
a computer, which when controlled by the access control program, is configured to:
 a) receive a request to upload patient-sourced medical data to an EMR access control system, the request including the patient-sourced medical data about a patient from the patient;
 b) store the patient-sourced medical data in an EMR in a patient-sourced data section of the EMR;
 c) modify the patient-sourced medical data using the access program based on a subset of patient information stored in a healthcare provider section of the EMR, the healthcare provider section consisting of information entered by a healthcare provider, wherein the patient has only restricted access to the data in the healthcare provider section to preserve the validity of the healthcare provider section data, the subset being defined by the healthcare provider;
 d) enter the modified information into the healthcare provider section; and
 e) return an information report to the patient based on the modified patient-sourced data,
wherein the subset defined by a healthcare provider is defined to exclude patient access to information in the healthcare provider section until the occurrence of a personal consultation between the patient and the healthcare provider, the exclusion being indicated by data and programmable rules in the electronic medical record of the healthcare provider.

20. The computer-implemented electronic medical record (EMR) access control system of claim 19 wherein modification of the patient-sourced medical data uses historical data about the patient held in the healthcare provider section.

21. The computer-implemented electronic medical record (EMR) access control system of claim 19 further including processing the patient-sourced data to provide data to the patient indicating a patient specific range of physiology values for the patient-sourced data based on medical data about the patient held in the healthcare provider section.

22. The computer-implemented electronic medical record (EMR) access control system of claim 19 further including testing the data for entry errors based on knowledge about the patient held in the healthcare provider section.

23. The computer-implemented electronic medical record (EMR) access control system of claim 22 wherein the patient is notified of the entry errors to permit re-entry of the patient-sourced medical data.

24. The computer-implemented electronic medical record (EMR) access control system of claim 19 wherein the processing of the patient-sourced data provides output to the patient indicating a medical issue.

25. The computer-implemented electronic medical record (EMR) access control system of claim 24 wherein the system provides the patient with prepared background information about the medical issue.

26. The computer-implemented electronic medical record (EMR) access control system of claim 24 wherein the access program provides the patient with clinical options for assisting in correcting the medical issue.

27. The computer-implemented electronic medical record (EMR) access control system of claim 24 wherein the patient is prompted to seek healthcare support.

28. The computer-implemented electronic medical record (EMR) access control system of claim 19 wherein a healthcare professional is notified of abnormal conditions indicated by the patient-sourced data to permit review of the patient-sourced data.

29. The computer-implemented electronic medical record (EMR) access control system of claim 28 wherein the healthcare professional is notified by a secure electronic message.

30. The computer-implemented electronic medical record (EMR) access control system of claim 19 wherein the patient-sourced data is selected from the group consisting of: patient's weight, blood glucose, blood pressure, pain level, previous health conditions, heart rate, temperature, last menstrual period, and dialysis status.

31. The computer-implemented electronic medical record (EMR) access control system, of claim 19 wherein the patient-sourced data from the patient is authenticated by a patient specific token.

32. The computer-implemented electronic medical record (EMR) access control system of claim 19 wherein the healthcare provider section holds medical data provided by different healthcare professionals for multiple patients.

33. The computer-implemented electronic medical record (EMR) access control system of claim 19 wherein the access program includes a web server and the patient-sourced data is received over the Internet from a web browser.

34. The computer-implemented electronic medical record (EMR) access control system of claim 19 wherein the patient-sourced data is entered into the healthcare provider section.

35. The computer-implemented electronic medical record (EMR) access control system of claim 34 wherein the patient-sourced data is further presented to a healthcare professional for validation prior to being entered into the healthcare provider section.

36. The computer-implemented electronic medical record (EMR) access control system of claim 19 wherein patient-sourced data is selected from a source consisting of machine-generated data from home healthcare appliances and patient-collected data manually input by a patient.

37. The computer-implemented electronic medical record (EMR) access control system of claim 19 wherein the subset defined by a healthcare provider is defined to exclude patient access to information pertaining to at least one medical condition identified by the programmable rules as being known to cause distress to the patient.

* * * * *